US011476057B2

(12) United States Patent
King et al.

(10) Patent No.: US 11,476,057 B2
(45) Date of Patent: Oct. 18, 2022

(54) INCREASING CAPACITANCE OF A CAPACITOR

(71) Applicant: Pacesetter, Inc., Sylmar, CA (US)

(72) Inventors: Justin King, Clemson, SC (US); Ralph Jason Hemphill, Sunset, SC (US); Timothy Marshall, Pickens, SC (US); David Bowen, Taylors, SC (US)

(73) Assignee: Pacesetter, Inc., Santa Clara, CA (US)

(*) Notice: Subject to any disclaimer, the term of this patent is extended or adjusted under 35 U.S.C. 154(b) by 757 days.

(21) Appl. No.: 16/502,900

(22) Filed: Jul. 3, 2019

(65) Prior Publication Data
US 2021/0005395 A1 Jan. 7, 2021

(51) Int. Cl.
H01G 9/00 (2006.01)
C25F 3/04 (2006.01)
C23F 1/20 (2006.01)
C23F 17/00 (2006.01)
H01G 9/055 (2006.01)
A61N 1/39 (2006.01)

(52) U.S. Cl.
CPC ......... *H01G 9/0029* (2013.01); *A61N 1/3956* (2013.01); *A61N 1/3981* (2013.01); *C23F 1/20* (2013.01); *C23F 17/00* (2013.01); *C25F 3/04* (2013.01); *H01G 9/055* (2013.01)

(58) Field of Classification Search
CPC .... C23F 17/00; C23F 1/26; C23F 1/22; C23F 1/20; C25F 3/08; C25F 3/04
See application file for complete search history.

(56) References Cited

U.S. PATENT DOCUMENTS

| | | | |
|---|---|---|---|
| 2,339,806 A * | 1/1944 | Pullen | C25F 3/20 205/682 |
| 6,858,126 B1 | 2/2005 | Hemphill et al. | |
| 9,842,702 B1 * | 12/2017 | Bowen | H01G 9/0029 |
| 9,852,849 B2 * | 12/2017 | Hemphill | C25F 3/14 |
| 2002/0162990 A1 * | 11/2002 | Johnson | C23F 1/20 252/175 |

* cited by examiner

Primary Examiner — Brian W Cohen

(57) ABSTRACT

A chemical etch is performed on a sheet of material. An electrochemical etch is performed on the sheet of material after the chemical etch is performed on the sheet of material. A capacitor is fabricated such that an electrode included in the capacitor includes material from the sheet of material after the electrochemical etch was performed on the sheet of material. In some instances, the chemical etch included at least partially immersing the sheet of material in an etch bath that includes molybdenum. Additionally or alternately, the chemical etch can be performed for a period of time less than 60 s.

13 Claims, 7 Drawing Sheets

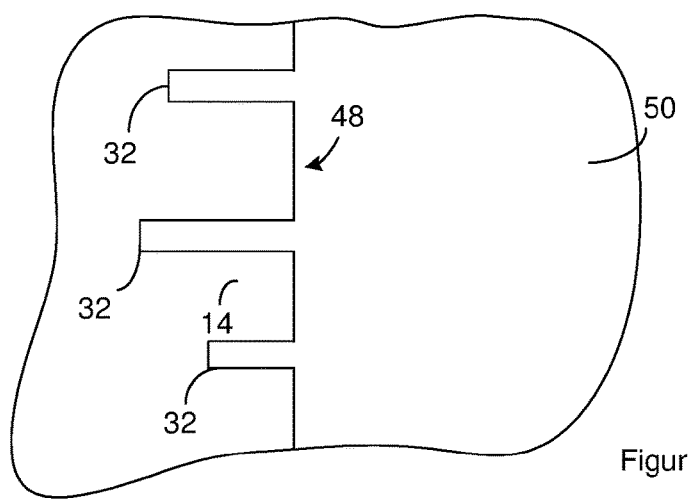
Figure 2E
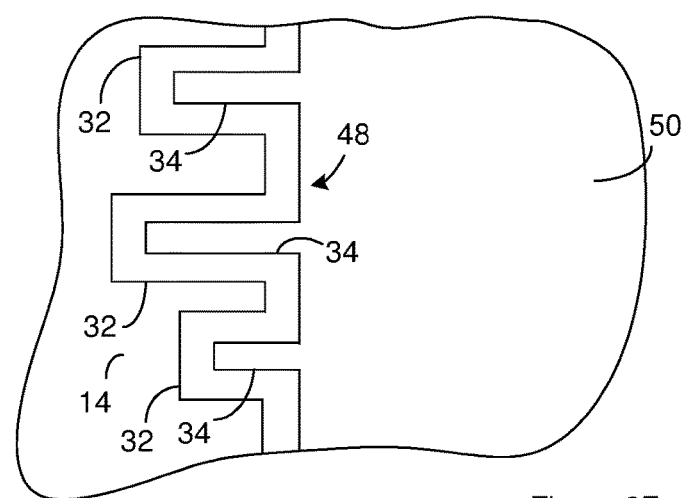
Figure 2F
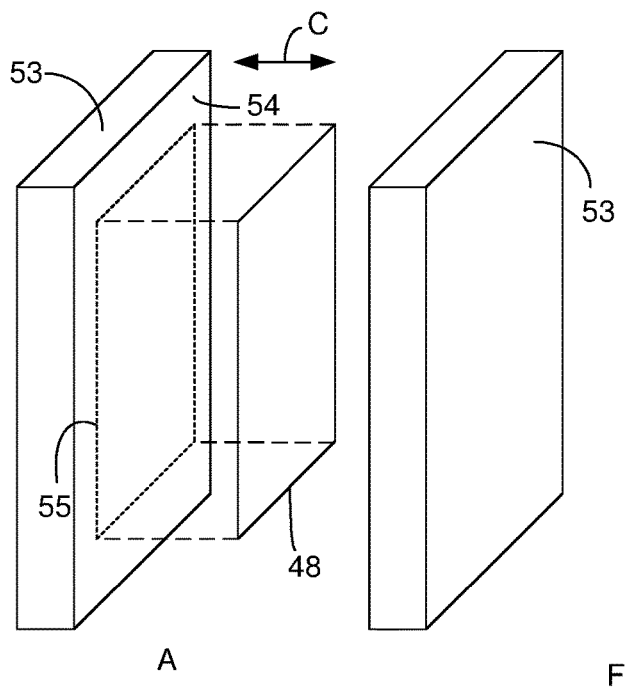 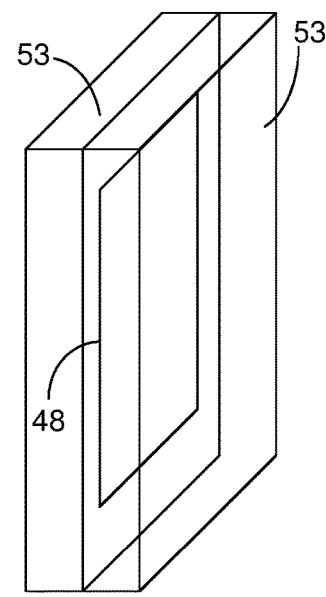
A                Figure 2G                B

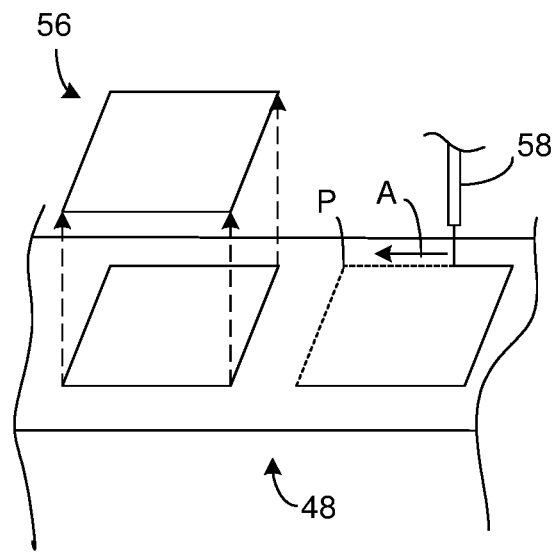
Figure 2H
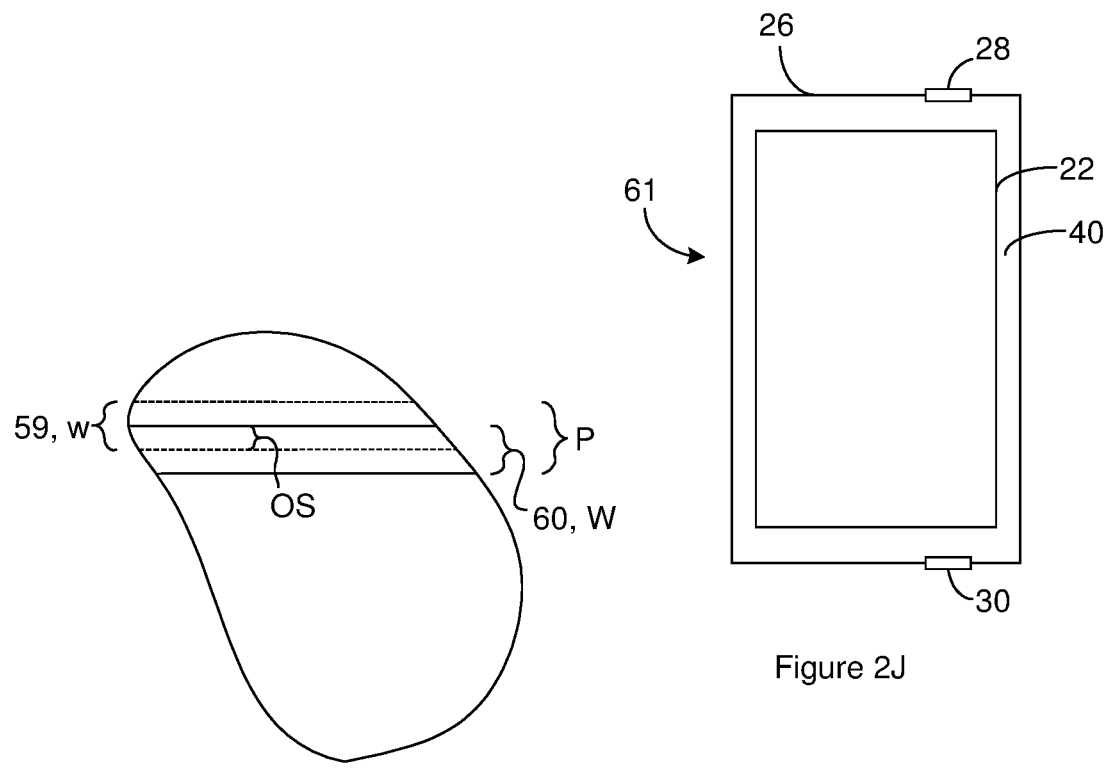
Figure 2I
Figure 2J

INCREASING CAPACITANCE OF A CAPACITOR

FIELD

The invention relates to electrochemical devices. In particular, the invention relates to electrodes in capacitors.

BACKGROUND

Capacitors are used in a variety of applications such as implantable cardioverter defibrillators (ICDs). In many of these applications, it is desirable to increase the capacitance per unit volume of the capacitor. Since the capacitance of an electrolytic capacitor increases with the surface area of its electrodes, increasing the surface area of the aluminum anode foil results in increased capacitance per unit volume of the capacitor. One method of increasing the surface area of the electrodes is to form channels in the electrodes. However, current methods of forming these channels can weaken the electrode and/or results in insufficient capacitance levels.

For the above reasons, there is a need for improved capacitor anodes.

SUMMARY

A chemical etch is performed on a sheet of material. An electrochemical etch is performed on the sheet of material after a chemical etch is performed on the sheet of material. A capacitor is fabricated such that one or more electrode(s) in the capacitor include material from the sheet of material after the electrochemical etch was performed on the sheet of material.

In some instances, the chemical etch included at least partially immersing the sheet of material in an etch bath that includes molybdenum. Additionally or alternately, the chemical etch can be performed for a period of time less than 45 seconds.

BRIEF DESCRIPTION OF THE FIGURES

FIG. 1A is a sideview of an anode that is suitable for use in the capacitor.

FIG. 1B is a cross-section of the anode shown in FIG. 1A taken along the line labeled B in FIG. 1A.

FIG. 1C is a sideview of a cathode that is suitable for use in the capacitor.

FIG. 1D is a cross-section of the cathode shown in FIG. 1C taken along the line labeled D in FIG. 1C.

FIG. 1E is a cross section of an electrode assembly where anodes are alternated with cathodes. The anodes and cathodes can be constructed according to FIG. 1A through FIG. 1D.

FIG. 1F is a schematic diagram of a capacitor that includes the electrode assembly of FIG. 1E positioned in a capacitor case.

FIG. 1G is a sideview of an interface between an anode and a cathode that are adjacent to one another in the capacitor of FIG. 1F.

FIG. 2A through FIG. 2J illustrate a method of generating an anode for use in a capacitor constructed according to FIG. 1A through FIG. 1G. FIG. 2A is a topview of a sheet of material from which the anode is constructed. The sheet of material can be a sheet of an anode metal.

FIG. 2B is a portion of a cross section of the sheet of material showing an interface between the side of the sheet of material and the atmosphere in which the sheet of material is positioned.

FIG. 2C illustrates the sheet of material of FIG. 2B after the formation of preliminary channels in the sheet of material.

FIG. 2D illustrates an electrochemical etch system that is suitable for performing an electrochemical etch or for performing a chemical etch and an electrochemical etch.

FIG. 2E illustrates the sheet of material of FIG. 2C after widening the preliminary channels.

FIG. 2F illustrates the sheet of material of FIG. 2C after formation of an anode metal oxide on the exposed surfaces of an anode metal.

FIG. 2G illustrates an example of a compression mechanism for performing a thermal compression operation on the sheet of material.

FIG. 2H illustrate an anode extracted from the sheet of material shown in FIG. 2F.

FIG. 2I is a topview of a portion of a sheet of material having a laser pathway with multiple different tracks.

FIG. 2J illustrates a capacitor that includes the anode of FIG. 2G.

DESCRIPTION

Fabricating an electrode for a capacitor includes a surface area enhancement phase where channels are created in a sheet of material. Creating the channels includes performing a chemical etch of a sheet of material followed by performing an electrochemical etch on the sheet of material. A capacitor is then fabricated such that one or more electrodes in the capacitor include material from the sheet of material.

Prior methods of creating the channels used an electrochemical etch but were not proceeded by the chemical etch. The inventors have surprisingly found that the use of the chemical etch before the electrochemical etch can increase the capacitance of electrodes by up to 10-11% and/or of the capacitor by up to 10-11%. As a result, the chemical etch can result in capacitors with increased capacitance. Alternately, the increased energy density can be used to fabricate capacitors with the about the same capacitance levels but with stronger electrodes.

In some instances, the chemical etch is galvanic corrosion. For instance, the chemical etch can be performed by fully or partially immersing the sheet of material in an etch bath that includes a bath metal in a liquid electrolyte. The sheet of material includes a metal such as an anode metal. The bath metal the metal in the sheet of material are selected to have electrode potential that cause galvanic corrosion of the metal in the sheet of material. For instance, when the sheet of material is an aluminum foil, the bath metal can be molybdenum. Without being bound to theory, the chemical etch is believed to increase the capacitance of the capacitor because by pitting the sheet of material so as to provide low energy cites at which tunnels can be generated during a subsequent electrochemical etch. The pitting is believed to result in a higher tunnel density than occurs without the chemical etch. The increased tunnel density may be the source of the increased capacity.

The inventors have surprisingly found that the duration of the chemical etch is related to the capacitance of the capacitor. For instance, the inventors have found that a change of only 8 seconds in the chemical etch bath duration can result in a 1.5% change in the capacitance of the capacitor. In some instances, the chemical etch duration is less than 60 seconds and can be in a range of 0 to 15 seconds.

Figure 1A:
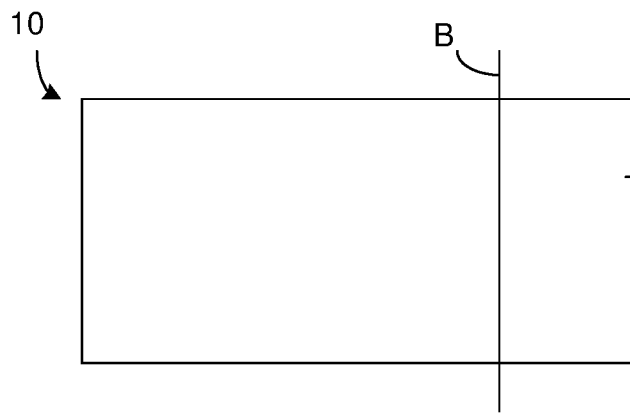
FIG. 1A through FIG. 1G illustrate the construction of a capacitor.
Figure 1B:
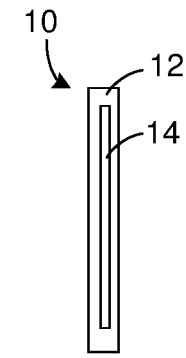

FIG. 1A through FIG. 1G illustrate the construction of a capacitor. FIG. 1A is a sideview of an anode 10 that is suitable for use in the capacitor. FIG. 1B is a cross-section of the anode 10 shown in FIG. 1A taken along the line labeled B in FIG. 1A. The anode 10 includes, consists of, or consists essentially of a layer of anode metal oxide 12 over a layer of an anode metal 14. Suitable anode metals 14 include, but are not limited to, aluminum, tantalum, magnesium, titanium, niobium, and zirconium. As illustrated in FIG. 1B, in some instances, the anode metal oxide 12 surrounds the anode metal 14 in that the anode metal oxide 12 is positioned on both the edges and the faces of the anode metal 14. Many anode metal oxides 12 can exist in more than one phase within the same material state (solid, liquid, gas, plasma). For instance, an anode metal oxide 12 such as aluminum oxide can be in a boehmite phase (AlO(OH)) that is a solid or in alpha phase corundum oxide phase ($\alpha$-$Al_2O_3$) that is also a solid.

Figure 1C:
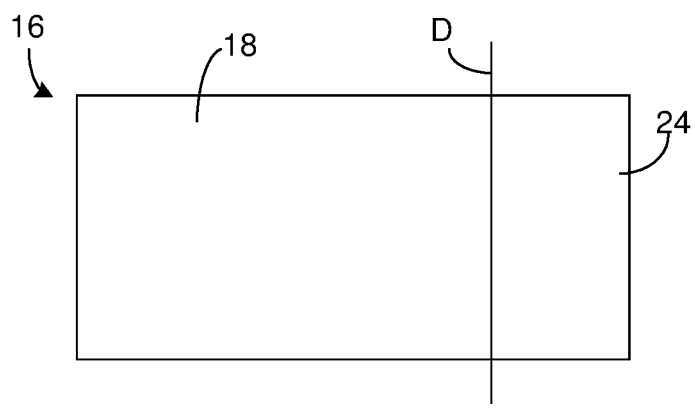
Figure 1D:
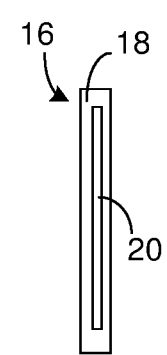

FIG. 1C is a sideview of a cathode 16 that is suitable for use in the capacitor. FIG. 1D is a cross-section of the cathode 16 shown in FIG. 1C taken along the line labeled D in FIG. 1C. The cathode 16 includes a layer of cathode metal oxide 18 over a layer of a cathode metal 20. Suitable cathode metals 20 include, but are not limited to, aluminum, titanium, and stainless steel. Although not illustrated, the cathode metal can be layer of material on a substrate. For instance, the cathode metal can be a titanium or titanium nitride coating on a substrate such as a metal and/or electrically conducting substrate. Examples of suitable substrates include, but are not limited to, aluminum, titanium, and stainless steel substrates. The cathode metal oxide 18 can be formed on the cathode metal 20 by oxidizing the cathode metal 20 in air. The cathode metal 20 can be the same as the anode metal 14 or different from the anode metal 14. In some instances, the cathode metal 20 and the anode metal 14 are both aluminum. As illustrated in FIG. 1D, in some instances, the cathode metal oxide 18 surrounds the cathode metal 20. For instance, the cathode metal oxide 18 is positioned over the edges and faces of the cathode metal 20.

Figure 1E:
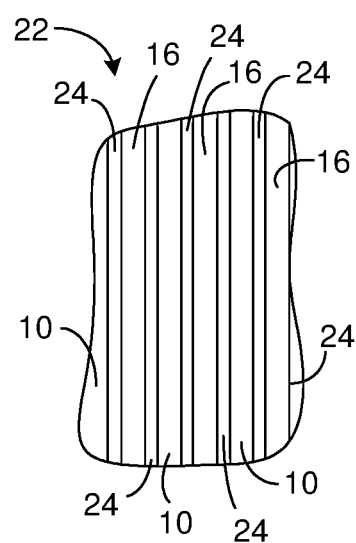

The anodes 10 and cathodes 16 are generally arranged in an electrode assembly 22 where one or more anodes 10 are alternated with one or more cathodes 16. For instance, FIG. 1E is a cross section of an electrode assembly 22 where anodes 10 are alternated with cathodes 16. The anodes 10 and cathodes 16 can be constructed according to FIG. 1A through FIG. 1D. A separator 24 is positioned between anodes 10 and cathodes 16 that are adjacent to one another in the electrode assembly 22. The electrode assembly 22 typically includes the anodes 10 and cathodes 16 arranged in a stack or in a jelly roll configuration. Accordingly, the cross section of FIG. 1E can be a cross section of an electrode assembly 22 having multiple anodes 10 and multiple cathodes 16 arranged in a stack. Alternately, the cross section of FIG. 1E can be created by winding one or more anodes 10 together with one or more cathodes 16 in a jelly roll configuration. However, as the anodes become more brittle due to increased surface area, it may not be practical or possible to form a jellyroll configuration. Suitable separators 24 include, but are not limited to, kraft paper, fabric gauze, and woven for non-woven textiles made of one or a composite of several classes of nonconductive fibers such as aramids, polyolefins, polyamides, polytetrafluoroethylenes, polypropylenes, and glasses.

Figure 1F:
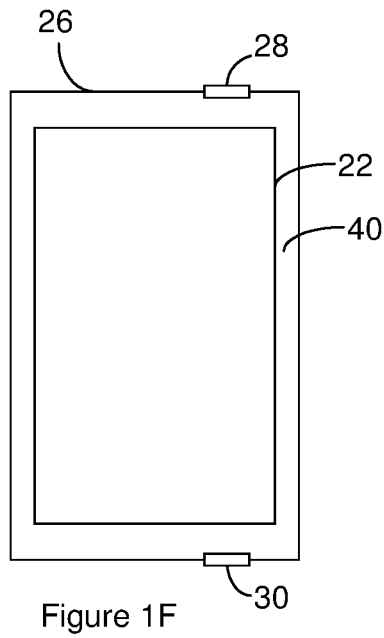

The electrode assembly 22 is included in a capacitor. For instance, FIG. 1F is a schematic diagram of a capacitor that includes the electrode assembly 22 of FIG. 1E positioned in a capacitor case 26. Although not illustrated, the one or more anodes in the electrode assembly 22 are in electrical communication with a first terminal 28 that can be accessed from outside of the capacitor case 26. The one or more cathodes 16 in the electrical assembly are in electrical communication with a second terminal 30 that can be accessed from outside of the capacitor case 26. In some instances, the one or more anodes include or are connected to tabs (not shown) that provide electrical communication between the one or more anodes and the first terminal 28 and the one or more cathodes 16 include or are connected to tabs (not shown) that provide electrical communication between the one or more cathodes 16 and the second terminal 30. The capacitor can include one or more electrical insulators (not shown) positioned as needed to prevent shorts-circuits within the capacitor.

Figure 1G:
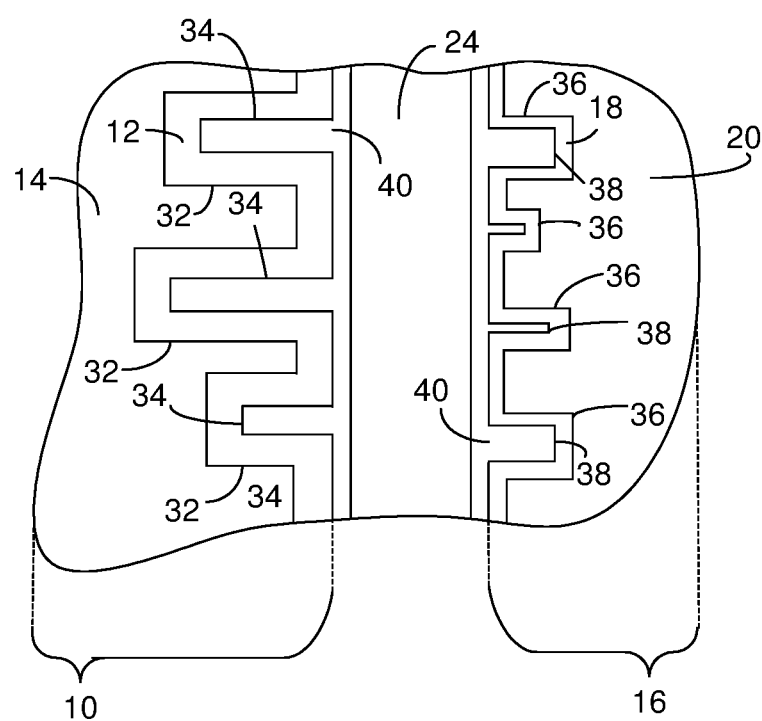

FIG. 1G is a sideview of an interface between an anode 10 and a cathode 16 that are adjacent to one another in the capacitor of FIG. 1F. The illustration in FIG. 1G is magnified so it shows features of the anode 10 and cathode 16 that are not shown in FIG. 1A through FIG. 1E. The face of the anode 10 includes channels 32 that extend into the anode metal 14 so as to increase the surface area of the anode metal 14. Although the channels 32 are shown extending part way into the anode metal, all or a portion of the channels 32 can extend through the anode metal. Suitable channels 32 include, but are not limited to, pores, trenches, tunnels, recesses, and openings. In some instances, the channels 32 are configured such that the anode has a number of channels/area greater than or equal to 30 million tunnels/$cm^2$. Increasing the number of channels has been shown to increase the brittleness of the anodes and/the sheet of material from which the anodes are extracted. Accordingly, increasing the surface area of the anode can result in a more brittle anode or sheet of material. The anode metal oxide 12 is positioned on the surface of the anode metal 14 and is positioned in the channels 32. The anode metal oxide 12 can fill the channels 32 and/or anode oxide channels 34 can extend into the anode metal oxide 12. However, it is generally not desirable for the anode metal oxide 12 to fill the channels 32 because filling the channels 32 can lead to reduced capacitance and electrical porosity.

The surface of the cathode 16 optionally includes cathode channels 36 that extend into the anode metal 14 so as to increase the surface area of the anode metal 14. Suitable cathode channels 36 include, but are not limited to, pores, trenches, tunnels, recesses, and openings. The cathode metal oxide 18 can be positioned on the surface of the cathode metal 20. When the cathode metal 20 includes cathode channels 36, the cathode metal oxide 18 can be positioned in the cathode channels 36. The cathode metal oxide 18 can fill the cathode channels 36 and/or cathode oxide channels 38 can extend into the cathode metal oxide 18.

An electrolyte 40 is in contact with the separator 24, the anode 10 and the cathode 16. The electrolyte 40 can be positioned in the cathode oxide channels 38. When the cathode metal 20 includes cathode oxide channels 38, the electrolyte 40 can be positioned in the cathode oxide channels 38. The electrolyte 40 can be a liquid, solid, gel or other medium and can be absorbed in the separator 24. The electrolyte 40 can include one or more salts dissolved in one or more solvents. For instance, the electrolyte 40 can be a mixture of a weak acid and a salt of a weak acid, preferably a salt of the weak acid employed, in a polyhydroxy alcohol solvent. The electrolytic or ion-producing component of the electrolyte 40 is the salt that is dissolved in the solvent.

A capacitor constructed according to FIG. 1A through FIG. 1G can be an electrolytic capacitor such as an aluminum electrolytic capacitor, a tantalum electrolytic capacitor or a niobium electrolytic capacitor. An electrolytic capacitor is generally a polarized capacitor where the anode metal oxide 12 serves as the dielectric and the electrolyte 40 effectively operates as the cathode 16.

Figure 2A:
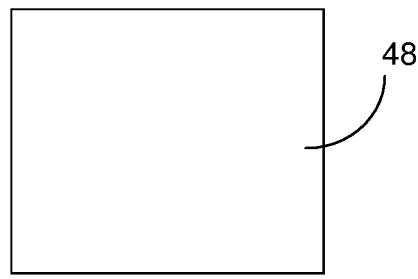
Figure 2B:
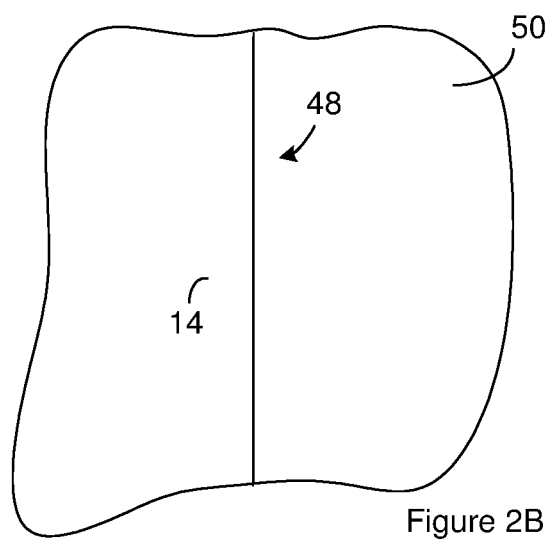
Figure 2C:
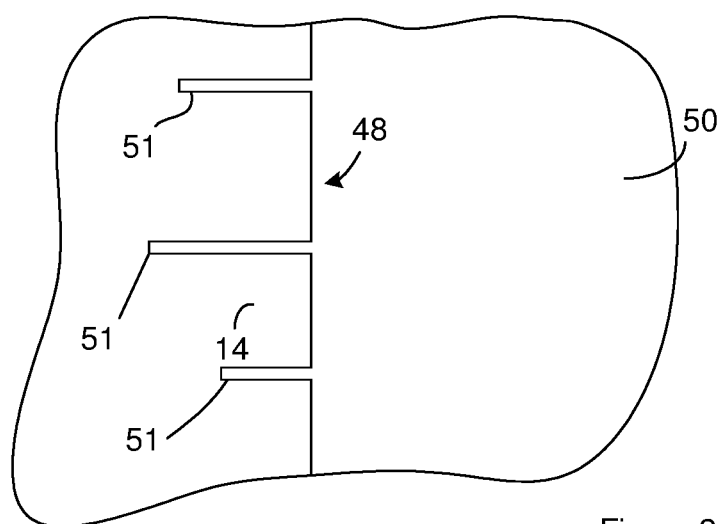

FIG. 2A through FIG. 2J illustrate a method of generating an anode for use in a capacitor constructed according to FIG. 1A through FIG. 1G. FIG. 2A is a sideview of a sheet of material 48. As will be evident below, one or more anodes are constructed from the sheet of material 48. The sheet of material 48 can be acquired either by fabrication or purchase from a supplier. FIG. 2A is a topview of the sheet of material 48 and shows a face of the sheet of material 48 positioned between edges of the sheet of material 48. FIG. 2B is a portion of a cross section of the sheet showing an interface between the face of the sheet of material 48 and the atmosphere 50 in which the sheet is positioned.

The sheet of material 48 can include, consist of, or consist essentially of the anode metal 14. In some instances the sheet of material 48 is a sheet of aluminum. In some instances, the sheet of material is aluminum and has one, more than one, or all of the characteristics selected from the group consisting of at least about 99.98% pure, at least about 80% crystal texture in the (1, 0, 0) direction, and a thickness in the range from about 85 microns to about 120 microns.

A surface area enhancement phase can be performed so as to increase the surface area of the sheet of material 48. For instance, the preliminary channels 51 can be formed in the sheet of material 48 so as to provide the sheet of material 48 with the cross section of FIG. 2C. The preliminary channels 51 can be created by chemical etching followed by an electrochemical etch. The chemical etch can be performed on the sheet of material 48 without applying an electrical potential across the sheet of material 48 so as to cause an electrical current to flow through the sheet of material 48.

The chemical etch can be an etch resulting from galvanic corrosion. For instance, the chemical etch can be performed by placing the sheet of material 48 fully or partially in a chemical etch bath such that at least one face of the sheet of material 48 is in direct physical contact with the chemical etch bath for a chemical etch duration. The chemical etch bath can be an electrolytic solution. At the expiration chemical etch duration, the chemical etch can be stopped. For instance, sheet of material 48 can be removed from the chemical etch bath or the electrochemical etch can be started.

Figure 2D:
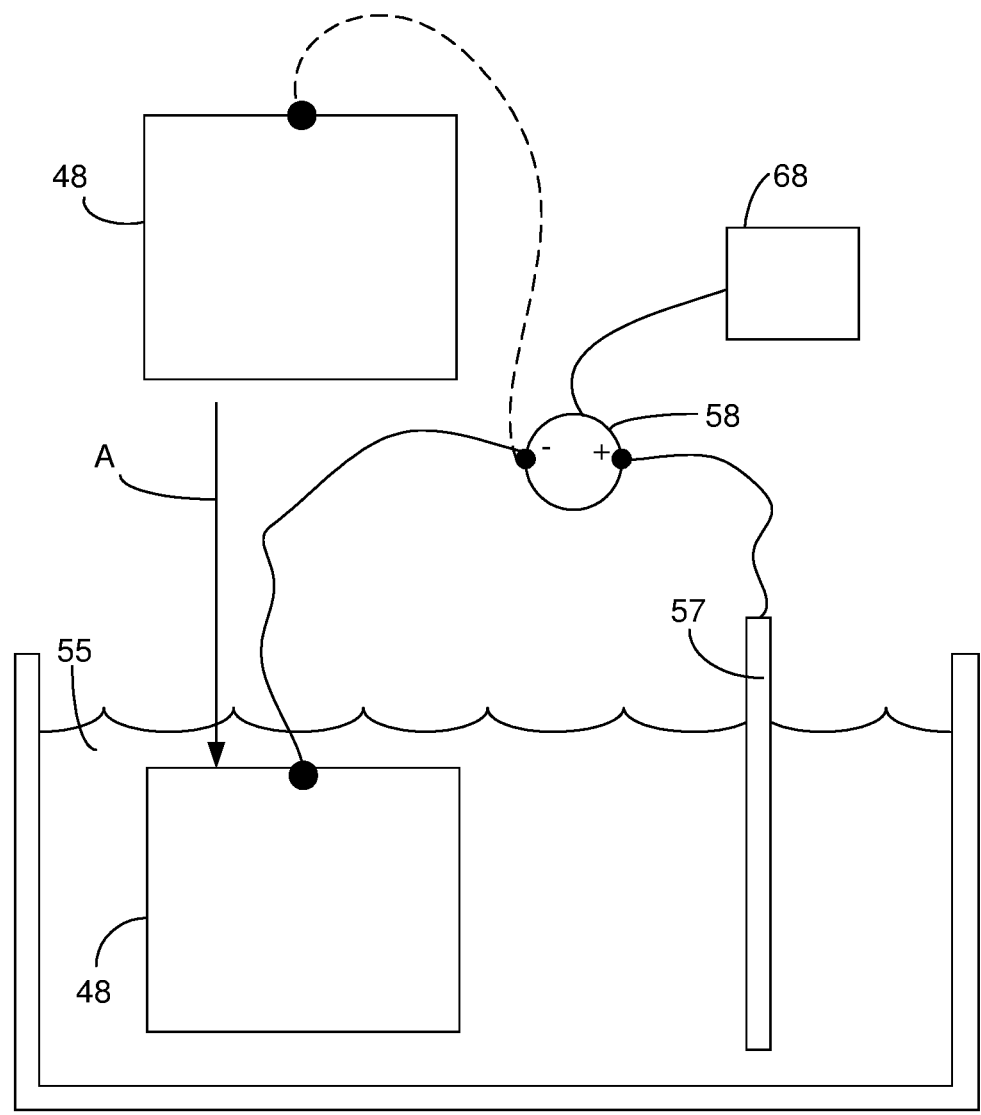

FIG. 2D illustrates an electrochemical etch system that is suitable for performing an electrochemical etch. The electrochemical etch system includes a reservoir that holds an etch bath 55 that can serve as the electrochemical etch bath. A cathode 57 is in contact with the etch bath 55. Suitable cathodes 57 include, but are not limited to, titanium, glassy carbon, and graphite.

As shown by the arrow labeled A in FIG. 2D, the sheet of material 48 is placed in electrical communication with a potential source 58 that is in electrical communication with the cathode 57. For instance, a wire or electrical cable can be clipped to the sheet of material 48. Suitable potential sources 58 include, but are not limited to, DC power sources such as a DC power supply, rectifier power supply, and a battery. The sheet of material 48 can be placed fully or partially in the etch bath 55 as illustrated by the arrow labeled A in FIG. 2D. The sheet of material 48 is placed in the etch bath 55 such that at least one face of the sheet of material 48 is in direct physical contact with the etch bath 55. The etch bath 55 can be a liquid.

The electrochemical etch is performed by using the potential source 58 to apply an electrical potential across the sheet of material 48 such that an electrical current passes through the sheet of material 48. The electrochemical etch is performed for an electrochemical etch duration. In some instances, the electrochemical etch is performed such that a constant current or substantially constant current flows through the sheet of material for the etch duration. Suitable electrochemical etch durations include, but are not limited to electrochemical etch durations greater than 30 seconds or 90 second and/or less than 2 minutes or 4 minutes. At or after occurrence of the electrochemical etch duration, the electrochemical etch can be stopped. For instance, the sheet of material 48 can be removed from the electrochemical etch bath and/or the application of the electrical potential across the sheet of material 48 can be stopped.

In some instances, the etch bath 55 serve as the electrochemical etch bath and the chemical etch bah. In these instances, the sheet of material 48 can be placed in electrical communication with the potential source 58 as shown in FIG. 2D. The sheet of material 48 can be placed fully or partially in the etch bath 55 as illustrated by the arrow labeled A in FIG. 2D. The sheet of material 48 is placed in the etch bath 55 such that at least one face of the sheet of material 48 is in direct physical contact with the etch bath 55. To perform the chemical etch, the sheet of material 48 can remain in the electrochemical etch bath for the chemical etch duration without the potential source applying the potential across the sheet of material 48 for the chemical etch duration. Upon expiration of the chemical etch duration, the potential source can be used to apply the electrical potential across the sheet of material 48 so as to perform the electrochemical etch as described above.

Suitable temperatures for the etch bath include, but are not limited to, temperatures greater than 70 or 78 C and/or less than 85 or 96 C during the chemical etch bath duration and/or during the electrochemical etch bath duration. Low temperatures during the chemical etch can require additional time to achieve the needed level of pitting while higher temperatures can result in an undesirably high level of pitting. During the electrochemical etch, the temperature can affect the tunnel morphology. For instance, temperature can affect tapering of the tunnels and/or the difficulty of removing etched materials from within the tunnels.

Electronics 68 can be in electrical communication with the electrochemical etch system. The electronics can control the operation of the electrochemical etch system. For instance, the electronics 68 can determine when the sheet of material 48 has been placed in the etch bath 55 and can begin the electrochemical etch upon expiration of the chemical etch duration. For instance, an operator can place the sheet of material in the etch bath. Once the sheet of material is in the desired location in the etch bath, the user can active a user interface such as pressing a button to indicate to the electronics that the that the sheet of material 48 is placed in the etch bath 55. In response, the electronics can start measuring the time of the chemical etch. Upon or after the electronics determining that the electrochemical etch duration has passed, the electronics can start the electrochemical etch by applying to the sheet of material 48 the electrical potential for the electrochemical etch.

One method that can be used to determine when the sheet of material has been placed in the etch bath 55 is to use the potential source to apply a test potential to the sheet of material 48. When the sheet of material 48 is placed in the etch bath 55, the test potential causes an electrical current to pass through the sheet of material 48. As a result, the electronics determine that the sheet of material 48 has been placed in the etch bath 55 in response to the presence of the electrical current through the sheet of material 48.

Once the electronics 68 determine that the sheet of material 48 has been placed in the etch bath 55, the electronics can stop the application of the test potential to the sheet of material for the remainder of the chemical etch duration and/or stop the flow of the electrical current through the sheet of material 48 for the remainder of the chemical etch duration. In some instances, the electronics 68 can continue to apply the test potential to the sheet of material for the remainder of the chemical etch duration. In some instances, there is a galvanic potential across the sheet of material in addition to the potential applied to the electronics. In some instances, the total of the test potential and/or the galvanic potential applied to the sheet of material 48 is low enough to prevent electrochemical etching of the sheet of material. Accordingly, the test potential and/or the galvanic potential applied across the sheet of material during the chemical etch can be less than 5% or 1% of the total electrical potential applied across the sheet of material during the electrochemical etch. For instance, the test potential and/or the galvanic potential electrical potential applied across the sheet of material during the chemical etch can be less than 6V, or IV. Additionally or alternately, in some instances, the test potential applied by the electronics and/or the galvanic potential can continue to drive an electrical current through the sheet of material 48 for the remainder of the chemical etch duration. In these instances, the level of electrical current through the sheet of material 48 is low enough to prevent electrochemical etching of the sheet of material 48. Accordingly, the electrical current passed through the sheet of material 48 during the chemical etch can be less than 5% or 1%, of the electrical current passed through the sheet of material during the electrochemical etch. For instance, the electrical current passed through the sheet of material during the chemical etch can be less than 0.02 amps/cm$^2$.

In some instances, at least one bath selected from the etch bath, the chemical etch bath, and the electrochemical etch bath includes one or more acids. Suitable acids include, but are not limited to, hydrochloric acid; mineral acids such as sulfuric, nitric, hydrobromic, and hydrofluoric acid; and other inorganic acids such as phosphoric acid; and organic acids such as formic, acetic, chloroacetic, trichloroacetic and trifluoroactic acid. Some of these acids such as sulfuric can act as an oxidizer and/or provides the desired viscosity levels.

The bath can include one or more secondary acids. Suitable secondary acids include, but are not limited to, nonafluorobutanesulfonic acid (FBSA) and salts of FBSA such as potassium nonafluorobutanesulfonic acid (KFBS). In some instances, the secondary acids act as a surfactant that can increase tunnel density. Suitable individual or collective concentrations for the one or more secondary acids include, but are not limited to, concentrations in a range of 2 parts per million (PPM), 5 parts per million (PPM), or 100 parts per million (PPM) to about 100 parts per million (PPM), 500 parts per million (PPM), or 1000 parts per million (PPM). In some instances, the individual or collective concentrations for the one or more secondary acids are less than 1000 parts per million (PPM).

The bath also includes one or more oxidizers. Suitable oxidizers for use in the present invention include, but are not limited to, sodium perchlorate. In some instance, a combination of sodium persulfate and sodium perchlorate is used. The individual or collective concentrations of the one or more oxidizers can be in the range of about 2 parts per million (PPM), 5 parts per million (PPM), or 100 parts per million (PPM) to about 100 parts per million (PPM), 500 parts per million (PPM), or 1000 parts per million (PPM). The individual or collective concentrations of the one or more oxidizers can be in a range of 1.5% by weight, 3.0% by weight, or 5.0% by weight to 5.5% by weight, 7.0% by weight, or 10% by weight.

The bath can include one or more bath metals selected such that the anode metal in the sheet of material is corroded by galvanic corrosion when the sheet of material is fully or partially immersed in the bath. Surprisingly, galvanic corrosion does not consume or substantially consume a bath metal such as molybedenum. When the sheet of material includes or consists of aluminum, or tantalum; molybdenum can serve as the bath metal and the bath can include one or more molybdenum-containing components.

The molybdenum-containing component can be elemental molybdenum or can be a compound that includes the molybdenum. A compound that includes the molybdenum can be neutral or can be charged. Suitable molybdenum-containing components include, but are not limited to, compounds with fewer than 5, or 15 atoms. In some instances, the molybdenum-containing component is dissolved in the bath and the molybdenum is present in the bath as a cation in one or more oxidation states selected from the group consisting of (I), (II), (III), (IV), (V), and (VI). Additionally or alternately, in some instances, the molybdenum-containing component includes the molybdenum linked directly to one or more components selected from a group consisting of oxygen, chloride, nitrogen, phosphorous, and sulfur. Examples include a molybdenum-containing component where the molybdenum is linked directly to a nitrogen in a nitrate, a phosphorus in a phosphate, and/or a sulfur in a sulfate. In some instances, the molybdenum-containing component is selected from a group consisting of molybdic acid, molybdenum trioxide, sodium molybdate dihydrate, molybdenum chloride, and molybdenum sulfide, molybdenum dioxide, and molybdenum chloride. Examples of the molybdenum-containing components are compounds with the molybdenum in the III, IV, V, or VI oxidation state. For instance, suitable molybdenum-containing components include, but are not limited to, molybdenum (VI) trioxide, sodium molybdate dihydrate, molybdenum (V) chloride, and molybdenum (IV) sulfide, molybdenum (IV) dioxide, AND molybdenum (II) chloride. The oxidation state of the molybdenum cations in the bath may be different from the oxidation state in the molybdenum-containing component. Suitable concentrations for the molybdenum in the bath include, but are not limited to, concentrations greater than 0 ppm, or 30 pp and/or less than 100 ppm, or 300 ppm.

The pH of the bath can affect the rate of galvanic corrosion. In some instances, the components of the bath are selected to provide the bath with a pH greater than 0, or 0.05 and/or less than 2, 2.5, or 4. One example of the bath includes 60 to 80 ppm molybdic acid, 0.62 wt % hydrochloric acid, 0.92 wt. % sulfuric acid, 3.5 wt. % sodium perchlorate, and 60 ppm nonafluorobutanesulfonic acid (FBSA). In some instances, the capacitance has started to drop as the pH exceeds 2.5.

As noted above, the inventors have surprising found a relationship between the chemical etch duration and the capacitance of an anode constructed from the sheet of material and/or of a capacitor that includes one or more anodes constructed from the sheet of material. Suitable chemical etch durations include, but are not limited to, times greater than 0.0 s, 3 s, and 4 s and/or less than 200 s, or 400 s. When the etch bath is a liquid electrolyte, the sheet of material includes or consists of aluminum, the bath metal is molybdenum, examples of the chemical etch duration include, but are not limited to, times greater than 0.0 s, 3 s, or 5 s and/or less than 15 s, 45 s, or 100 s.

In some instances, the surface area enhancement phase also includes widening of the preliminary channels 51. Widening of the preliminary channels can reduce or stop the anode metal oxide 12 from filling the channels 32. For instance, the distance across the preliminary channels 51 on the sheet of FIG. 2C can be increased to provide a sheet of material 48 having the channels 32 shown in the cross section of FIG. 2E. In some instances, the preliminary channels 51 are fabricated and widened so as to remove more than 52% or 60% of the sheet of material 48 from the sheet of material 48 and/or to create more than 30 million channels/cm$^2$ of the sheet of material 48.

Suitable methods for widening the preliminary channels 51 include, but are not limited to, chemical and electrochemical processes. In one example of the widening process, widening of the preliminary channels 51 includes immersing at least a portion of the sheet of material 48 in an electrolyte solution that includes, consists of, or consists essentially of a chloride or nitrate. Additional examples of suitable methods for widening of the preliminary channels 51 and/or additional details about the above methods of widening preliminary channels 51 can be found in U.S. patent application Ser. No. 05/227,951, filed on Feb. 22, 1972, granted U.S. Pat. No. 3,779,877, and entitled "Electrolytic Etching of Aluminum Foil;" U.S. patent application Ser. No. 06/631,667, filed on Jul. 16, 1984, granted U.S. Pat. No. 4,525,249, and entitled "Two Step Electro Chemical and Chemical Etch Process for High Volt Aluminum Anode Foil;" U.S. patent application Ser. No. 11/972,792, filed on Jan. 11, 2008, granted U.S. Pat. No. 8,535,527, and entitled "Electrochemical Drilling System and Process for Improving Electrical Porosity of Etched Anode Foil;" U.S. patent application Ser. No. 10/289,580, filed on Nov. 6, 2002, granted U.S. Pat. No. 6,858,126, and entitled "High Capacitance Anode and System and Method for Making Same;" and U.S. patent application Ser. No. 10/199,846, filed on Jul. 18, 2002, granted U.S. Pat. No. 6,802,954, and entitled "Creation of Porous Anode Foil by Means of an Electrochemical Drilling Process;" each of which is incorporated herein in its entirety.

The anode metal oxide 12 is formed on the anode metal 14 that is exposed in the sheet of material 48. For instance, the anode metal oxide 12 can be formed on the anode metal 14 that is exposed in FIG. 2E so as to provide a sheet of material 48 according to FIG. 2F. The anode metal oxide 12 extends into the channels 32 so as to provide anode oxide channels 34. Forming the anode metal oxide 12 on the exposed anode metal 14 can include converting a portion of the existing anode metal 14 to the anode metal oxide 12 or adding a layer of the anode metal 14 over the previously existing anode metal 14. Converting a portion of the existing anode metal 14 to the anode metal oxide 12 can include reacting the anode metal 14 with a component such as oxygen. The anode metal oxide 12 is formed so the anode metal oxide 12 is in a first phase of the anode metal oxide 12. As an example, when the anode metal 14 is aluminum, the boehmite phase (AlO(OH)) of aluminum oxide is formed as the anode metal oxide 12. The first phase of the anode metal oxide 12 is desirable for the final capacitor. For instance, the first phase of the anode metal oxide 12 generally serves as the dielectric for the capacitor.

An example of a suitable method of forming the anode metal oxide 12 on the anode metal 14 includes an optional hydration layer formation operation, one or more oxide formation operations, and one or more thermal treatments.

The hydration layer formation operation forms a hydration layer in direct contact with the anode metal 14. The hydration layer can include, consist of, or consist essentially of the anode metal 14, hydrogen, and water. For instance, the hydration layer can include, consist of, or consist essentially of a hydrate of the anode metal 14. When the anode metal 14 is aluminum, the hydration layer can include, consist of, or consist essentially of aluminum hydrate.

In some instances, the hydration layer is formed on the anode metal 14 by placing the sheet of material 48 in a bath liquid that includes, consists of, or consists essentially of water. In one example, the bath liquid is de-ionized water. The bath liquid may be held at a temperature between 60° C. and 100° C. In some instances, the bath liquid is maintained at about 95° C. The sheet of material 48 can remain in the bath liquid for a formation time. The formation time can be greater than 1 minute and/or less than 20 minutes. The hydration can help form a better quality oxide during the one or more oxide formation operations.

An example of a suitable oxide formation operation includes, but is not limited to, mechanisms that convert existing anode metal 14 to anode metal oxide 12 such as anodic oxidation. In anodic oxidation, the sheet of material 48 is placed in an electrolytic bath while a positive voltage is applied to the sheet of material 48. The thickness of the layer of anode metal oxide 12 can be increased by increasing the applied voltage. When the anode metal 14 is aluminum, anodic oxidation forms a layer of the boehmite phase of aluminum oxide (AlO(OH)) on a layer of aluminum. In one example of anodic oxidation, the anode metal oxide 12 is formed by placing the sheet of material in citric acid while a positive voltage of 400-550 volts is applied to the sheet of material for a period of time between 30 minutes to 150 minutes. Additionally or alternately, the electrical current that results from the applied voltage can be monitored and the sheet of material can be removed from the electrolytic solution in response to the electrical current exceeding a treatment threshold.

The layer of oxide formed during the first oxide formation operation performed on the sheet of material replaces and/or consumes the hydration layer formed during the hydration layer formation operation. As a result, the hydration layer is generally not present on the layer of material after the first oxide formation operation.

In some instances, the thermal treatments are each performed after an oxide formation operation. The thermal treatments elevate the temperature of the sheet of material enough to drive out water from the layer of anode metal oxide 12 formed during the previous oxide formation operation(s). The removal of this water has been shown to decrease the leakage of capacitors. However, it is not desirable to remove all of the water from the layer of anode metal oxide 12. Additionally, applying high levels of thermal energy to the sheet of material can increase the level of deformation in a capacitor that includes an electrode made from the sheet of material. As a result, reducing the amount of thermal energy applied to the sheet of material while removing this water may lead to both decreased leakage and decreased deformation.

A suitable thermal treatment includes one or more thermal compression operations. An example of a suitable thermal compression operation is compressing the sheet of material between surfaces for a compression time with at least one of the surfaces having an elevated temperature during the compression.

FIG. 2G illustrates an example of a compression mechanism for performing a compression operation. The compression mechanism includes two compression members. In FIG. 2G, a metal plate serves as each of the compression members. Each of the compression members includes a compression surface that is in direct contact with the sheet of material during the compression operation. A contact portion of each compression surface is the portion of the surface that is in contact with the sheet of material during the compression operation. The location of the contact portion on one of the compression members in diagram A of FIG. 2G is illustrated by dashed lines.

As is evident from the arrow labeled C in FIG. 2G, the compression members can be moved relative to one another. For instance, a first one of the compression members can be immobilized while the second compression member is moved relative to the first compression member. Alternately, both of the compression members can be moved.

To prepare for the compression operation, the sheet of material is placed between the compression members as shown in diagram A of FIG. 2G. The compression members are then moved relative to one another so the contact portion of each compression surface is in direct physical contact with the sheet of material as shown in diagram B of FIG. 2G. The compression surfaces apply pressure to the sheet of material during the compression operation. The compression operation continues for the compression time that is desired for the compression operation. After the compression time associated with the last compression operation is reached, the compression members can be moved apart and the sheet of material removed from between the compression members.

Although FIG. 2G shows the compression members as plates, the compression members can be other components. For instance, one of the compression members can be the side of an oven or the side of some other structure. Additionally or alternately, the compression members can be different structures. For instance, one of the compression members can be a plate as shown in FIG. 2G while another compression member is a side of an oven.

Although FIG. 2G shows the compression members as being independent of one another, the compression members may be physically connected to one another. For instance, the compression members can be hinged or can be different parts of a medium that is connected by a fold.

One or more of the compression members apply thermal energy to the sheet of material during a compression operation. For instance, the one or more compression members can heat the sheet of material during a compression operation. As an example, the contact portion of one or more of the compression surface can be at a compression temperature that is above room temperature. One or more of the compression members can include a heating mechanism for bringing the contact portion of a compression surface to the desired compression temperature. For instance, a resistive heater can be mounted on a plate that serves as a compression member. Alternately, a plate that serves as a compression member can include one or more channels through which a heated fluid is flowed. In some instances, the heating mechanism for bringing one or more of the compression surfaces to the desired compression temperature can be external to one or more of the compression members. For instance, the compression members can be located in an oven before and during the compression treatment. As an example, the compression members illustrated in FIG. 2G can be located in an oven before and during the compression treatment. The oven can be maintained at the compression temperature in order to keep the temperature of the contact portion of the compression surfaces at the desired compression temperature.

Each of the compression operations in a thermal treatment is performed for a compression time. The compression times associated with different compression operations can be the same or different. In some instances, the compression time is not long enough for the temperature of the sheet of material to reach the compression temperature. Accordingly, the temperature of the sheet of material at the end of the compression operation (final operation temperature) can be different from the compression temperature.

During a compression operation, a suitable pressure for applying to the sheet of material (compression pressure) is a pressure greater than 0.1 once per square inch or 1 once per square inch and/or less than 1.0 psi or 5.0 psi. During a compression operation, a suitable compression temperature for applying to the sheet of material is a temperature greater than 200° C., or 300° C., and/or less than 600° C., or 800° C. In some instances, the maximum temperature of the sheet of material during a compression operation is greater than 200° C., or 300° C., and/or less than 600° C., or 800° C. Suitable compression times include, but are not limited to, compression times greater than 1 second, 5 seconds and/or less than 10 seconds, 1 minute or ten minutes. In some instances, the compression pressure and/or compression temperature are held constant for the compression time during a compression operation.

In one example, a thermal treatment includes at least two compression operations performed at different pressure levels. A first one of the compression operations can be a low pressure compression and a second one of the compression operations can be a high pressure compression. The low pressure compression is performed at a lower compression pressure than the high pressure compression. In some instances, the high pressure compression is performed immediately after the low pressure compression without removing the sheet of material from between the compression members and without other compression operations being performed between the low pressure compression and the high pressure compression.

The low pressure compression can take advantage of the direct physical contact between the compression members and the sheet of material in order to quickly elevate the temperature of the sheet of material toward a final operation temperature that is desired for the start of the high pressure compression. Suitable compression pressures for the low pressure compression include, but are not limited to, pressures greater than 0.1 once per square inch or 1 once per square inch and/or less than 0.1 psi or 0.5 psi. Suitable compression temperatures for the low pressure compression include, but are not limited to, temperatures greater than 200° C., or 300° C., and/or less than 600° C., or 800° C. Suitable final operation temperatures for the low pressure compression include, but are not limited to, temperatures greater than temperatures greater than 200° C., or 300° C., and/or less than 600° C., or 800° C. Suitable compression times for the low pressure compression include, but are not limited to, times greater than 1 second, 5 seconds and/or less than 10 seconds, 1 minute or ten minutes. In some instances, the sheet of material is at or near room temperature before the low pressure compression. In some instances, the compression pressure and/or compression temperature are held constant or substantially constant for the compression time during the low pressure compression.

The high pressure compression can be performed for a duration that drives out the water from the layer of anode metal oxide 12 and/or that causes cracks to form in the anode metal oxide 12. Suitable compression pressures for the high pressure compression include, but are not limited to, pressures greater than 0.5 psi and/or less than 1.0 psi or 2.0 psi. Suitable compression temperatures for the high pressure compression include, but are not limited to, temperatures greater than 200° C., or 300° C., and/or less than 600° C., or 800° C. Suitable compression times for the high pressure compression include, but are not limited to, times greater than 1 second, 2 seconds and/or less than 10 seconds, 1 minute or ten minutes. In some instances, the compression temperatures for the high pressure compression is the same as the compression temperature for the low pressure compression. In some instances, the compression pressure and/or compression temperature are held constant or substantially constant for the compression time during the low pressure compression.

The increase in pressure between the low pressure compression and the high pressure compression can be done slowly. For instance, the increase in pressure can be at a rate greater than 0.0 psi/minute or 0.05 psi/min and/or less than 0.5 psi/min or 2 psi/min.

Various features of the method of forming the sheet of material as disclosed in the context of FIG. 2A through FIG. 2G cause the sheet of material to warp. For instance, the channels 32 are generally not evenly distributed across the sheet of material. Further, the morphology of these channels (i.e. straight channels, branched channels, etc.) is also not evenly distributed across the sheet of material. Additionally, forming the anode metal oxide 12 during the one or more oxide formation operations generally causes the sheet of material to shrink. For instance, the one or more oxide formation operations performed while forming the anode metal oxide 12 cause the volume of the sheet of material to decrease by as much as 15%. In some instances, the one or more oxide formation operations performed while forming the anode metal oxide 12 cause the volume of the sheet of material to decrease by more than 0.5%, or 1.5% and/or less than 4.5%, or 15%. The uneven distribution of the channels 32 combined with shrinkage of the sheet of material while forming the anode metal oxide 12 in these channels 32 causes warping of the sheet of material. Other sources of warping include, but are not limited to, the high voltages applied to the sheet of material during any anodic oxidation operations. Warped sheet of material tend to have multiple different peaks and valleys. In some instances, the peaks and valleys have widths on the order of 0.1 to 0.5 inches.

The thermal compression(s) in the thermal treatment can reduce the warping on of the sheet of material. The elevated temperature combined with the compression causes the sheet of material to adopt the shape of the interface between the contact portions of each compression surfaces. For instance, in FIG. 2G, the contact portions are each flat or planar. As a result, when the sheet of material adopts the shape of the interface, the sheet of material becomes flat or planar.

In some instances, one or more of the thermal treatments used while forming the anode metal oxide excludes a compression operation. For instance, as few as one of the thermal treatments performed while forming the anode metal oxide can include a compression operation while all other thermal treatments each exclude a compression operation. An example of a thermal treatment that excludes compression can include placing a sheet of material in an oven at a thermal treatment temperature for a thermal treatment time but without compression of the sheet of material. Suitable thermal treatment temperatures include, temperatures greater than 100° C., or 300° C. and/or less than 600° C., or 800° C. Suitable thermal treatment times include, times greater than 10 second, or 30 seconds, 3 minutes and/or less than 5 minutes, or 20 minutes.

When the method of forming the anode metal oxide 12 on the anode metal 14 includes a hydration layer formation operation, the hydration layer formation operation can be performed before the one or more oxide formation operations and before the one or more thermal treatments. When the method of forming the anode metal oxide 12 includes multiple oxide formation operations, the one or more thermal treatment can be alternated with the oxide formation operations. When the method of forming the anode metal oxide 12 on the anode metal 14 includes a hydration layer formation operation, the first oxide formation operation can be performed between the hydration layer formation operation and the first thermal treatment. Additionally or alternately, the last oxide formation operation can be performed after the last thermal treatment or the thermal treatment can be performed after the last oxide formation operation. In one example of the method of forming the anode metal oxide 12, the first oxide formation operation is performed between a hydration layer formation operation and the first thermal treatment; the one or more thermal treatment are alternated with the one or more oxide formation operations; and the last oxide formation operation is performed after the last thermal treatment. In another example of the method of forming the anode metal oxide 12, the first oxide formation operation is performed between a hydration layer formation operation and the first thermal treatment; the one or more thermal treatment are alternated with the one or more oxide formation operations; and the last thermal treatment operation is performed after the last oxide formation.

FIG. 2A through FIG. 2G illustrate a method of using fabrication to acquire a sheet of material 48 having a first phase of an anode metal oxide 12 on an anode metal 14. Alternately, any stage of the sheet of material 48 shown in FIG. 2A through FIG. 2G can be acquired by purchase from a supplier.

One or more anode precursors 56 are extracted from the sheet of material 48. Accordingly, a portion of the sheet of material 48 serves as the anode precursor 56. Suitable methods of removing an anode precursor 56 from the sheet of material 48 include, but are not limited to cutting the anode precursor 56 out of the sheet of material 48. A suitable method of cutting the anode precursor 56 out of the sheet of material 48 include mechanical cutting method such as die cutting where the anode precursor is punched or stamped from a sheet of material using a mechanical die. Another suitable method of cutting the anode precursor 56 out of the sheet of material 48 includes no-contact cutting methods such as laser cutting of the anode precursor 56. FIG. 2H illustrates use of a laser 58 to cut anode precursors 56 out of a sheet of material 48 constructed according to FIG. 2G.

The flat or planar shape of the sheet of material provided by thermal compression can improve the cutting processes. Mechanical cutting of a warped sheet of material can cause the sheet of material to move in response to the cutting operation. Laser cutting of a warped sheet of material causes the distance between the focal point and the sheet of material to change across the sheet of material. As a result, cutting of warped sheets of material provides inconsistent results. The flattening of the sheet of material provided by thermal compression can increase the consistency of the cutting results.

As noted above, laser cutting may provide an increase in yield and efficiency when compared with mechanical cutting methods. Laser cutting of the sheet of material can cause melted portions of the sheet of material to solidify and stay on the resulting anode precursor. Alternately, portions of the sheet can redeposit on the resulting anode precursor during the laser cutting process. These excess materials can be reduced by using a pulsed laser beam. The short pulse durations are possible with pulsed lasers can provide very high peak powers for moderately energetic pulses. The increased peak power can provide vaporization of the sheet of material during the laser cutting process. This vaporization can eject the material from any recess or trench created in the sheet of material through the top of the sheet of material. Since the material is ejected from the sheet of material, the material is not available to re-solidify or re-deposit on the sheet of material.

In some instances, the duration of the pulse is greater than 0 s, or a femtosecond ($10^{-15}$ s) and/or less than a microsecond ($10^{-6}$ s). In one example, the duration of the pulse is greater than 100 femtoseconds and less than 900 femtoseconds. The time between pulses is inversely related to the pulse frequency. Suitable pulse frequencies can be greater than 0 Hz, or 100 Hz, and/or less than 2000 kHz. In one example, the pulse frequency is in a range of 200 kHz to 600 kHz. In some instances, the duration of the pulse is greater than 0 s, or a femtosecond ($10^{-15}$ s) and/or less than a microsecond ($10^{-6}$ s) and the pulse frequency is greater than 0 Hz, or 100 Hz, or 100 kHz and/or less than 2000 kHz.

The power density of the laser beam at the sheet of material can be at a level that a single pulse elevates the temperature of the sheet of material above the boiling point of the anode metal and vaporizes the anode metal. In some instances, power density of the laser beam is such that at least a portion of the sheet of material that is illuminated by the laser reaches the boiling point of the anode metal and vaporizes in a period of time less than or equal to the duration of one pulse when the illuminated portion of the sheet of material is at temperature (23° C. or 25° C.) before the pulse. In an example where the anode metal is aluminum, the pulse duration is 820 femtoseconds, the pulse frequency is 400,000 pulses per second, and the laser beam has a power density $7.99 \times 10^{11}$ W/cm$^2$ at the surface of the sheet of material. Suitable power densities include, but are not limited to, power densities greater than 0 W/cm$^2$, $1 \times 10^{11}$ W/cm$^2$, or $2 \times 10^5$ W/cm$^2$ and/or less than $9 \times 10^{11}$ W/cm$^2$, or $2 \times 10^5$ W/cm$^{12}$. The combination of elevated power densities and reduced pulse durations reduces the amount of heat transferred to the sheet of material. However, adjusting these parameters may not be sufficient to address the increase in deformation that can result from using laser cutting of the anodes rather than stamped or punched cutting of the anodes.

The path of the laser beam across the face of the sheet of material can be controlled by electronics and/or software. The electronics and/or software can move the laser beam relative to the sheet of material and/or the sheet of material relative to the laser beam. In FIG. 2H, the solid lines and the dashed lines that show the outline of an anode precursor in the sheet of material represent the laser beam pathway during the process of cutting the anode precursor from the sheet of material. As a result, the laser is incident on the anode metal oxide during at least a portion of the laser cutting.

Tuning the characteristics for the laser beam path across the sheet of material can also reduce the leakage and deformation to or even below the levels associated with stamping or punching of anodes. For instance, the rate at which the beam is scanned across the sheet of material can be tuned. Faster scan rates reduce the amount of energy that is absorbed by the anode precursor. In some instances, the laser beam is scanned across the sheet of material at a rate greater than 0 mm/sec, 100 mm/sec, or 600 mm/sec, and/or less than 900 mm/sec, or 1100 mm/sec.

Reducing the spot size can also reduce the amount of thermal energy transferred to the sheet of material. Suitable spot sizes include, but are not limited to, spot having a diameter or major axis greater than 10 microns, 30 microns and/or less than 50 microns, or 150 microns. Additionally or alternately, the spot size can be selected to produce spot overlaps less than 100%. A spot is the area of the sheet of material illuminated by the laser beam during a pulse. Spot overlap is the overlap of a spot with the spot provided by the previous pulse. Suitable spot overlaps include spot overlaps greater than 70%, or 90% and/or less than 100%. The spot size can be selected to provide these levels of spot overlap when combined with the above scan rates and pulse frequencies.

Increasing the beam scan rate can reduce the depth that the laser beam cuts into the sheet of material. As a result, multiple passes of the laser beam along a pathway may be necessary in order to completely cut the anode precursor out of the sheet of material. This result is evident in the pathway labeled P FIG. 2H. The pathway includes dashed lines that indicate where the laser beam has cut into the sheet of material without cutting through the sheet of material. The pathway also includes solid lines that indicate the portion of the anode precursor outline where the laser beam has cut through the sheet of material. Additionally, the arrow labeled A indicates the travel direction travel for the laser beam relative to the anode precursor. At the start of the laser cutting, the laser beam may be incident on the anode metal oxide. Once the laser beam has cut through the anode metal oxide, the laser beam is incident on the anode metal.

The need for multiple passes of the laser beam in order to cut through the sheet of material means that each location along the beam pathway is not exposed to the leaser beam energy for a pass interval. The pass interval can be the time between passes of the laser beam and/or can be the period of time that passes between each point along the pathway being exposed to the laser beam. Suitable pass intervals include, but are not limited to, pass intervals more than 0.1 seconds per pass and/or less than 3 seconds per pass. In some instances, the pass interval is selected such that more than 5, or 10 and/or less than 100 passes of the laser beam around the entire outline of the anode precursor are required to completely extract an anode precursor from the sheet of material.

The laser pathway can includes multiple different tracks. FIG. 2I is a topview of a portion of a sheet of material 48. A portion of a laser pathway on the sheet of material is labeled P. The laser pathway includes a first track 59 represented by dashed lines and a second track 60 represented by solid lines. The first track 59 represents the track that the laser follows during a pass along the laser pathway. The second track 60 represents the track that the laser follows during a different pass along the laser pathway. The first track 59 has a width labeled w and the second track 60 has a width labeled W. When the first track 59 and the second track 60 are followed by the same laser or by lasers with the same spot size, the width of the first track 59 will be the same or about the same as the width of the second track 60.

The second track 60 is offset from the first track 59 by a distance labeled OS in FIG. 2. The amount of offset can be selected such that the second track 60 partially overlaps the first track 59 as shown in FIG. 2I. The use of partially overlapping tracks while laser cutting the anode precursor widens the trench that the laser forms in the sheet of material to a width larger than the spot diameter. The cutting of a wider trench can reduce the amount of thermal energy that is applied to previously formed surfaces in the trench. The track overlap percentage can be the overlap distance divided by the width of the overlapped track. Suitable track overlap percentages include, but are not limited to, track overlap percentages greater than 25% or 30% and/or less than 50% or 75%. The offset distance can be a function of spot size. For instance, when the spot size has a diameter of 40 microns, a suitable offset distances can be any distance between 0 and 40 microns such as 10 to 30 microns.

In some instances, the different tracks extend around the perimeter of the anode and/or surround the perimeter of the anode. For instance, the entire length of the laser pathway shown FIG. 2H can include two tracks that partially overlap as shown in FIG. 2I. In other words, the laser pathway of FIG. 2I can represent the laser pathway of any straight portion of the laser pathway shown FIG. 2H. Accordingly, the laser can trace all, or substantially all, of the anode perimeter along one track and later trace all, or substantially all, of the anode perimeter along another track that partially overlaps the prior track as described above. Alternately, different tracks can partially overlap along one or more portions of the anode perimeter but completely overlap along one or more other portions of the anode perimeter.

Although the laser pathway in FIG. 2I is illustrated as having two tracks, the laser pathway can include a single track or more than two tracks. During the laser cutting process, a track can be followed once or more than once. For instance, when a laser pathway includes two tracks as is shown in FIG. 2, the laser can alternate between different tracks on subsequent passes. As an example, the laser can follow the first track 59, the second track 60, the first track 59, the second track 60, and so on until the trench extends through the sheet of material and the anode precursor is extracted from the sheet of material.

In some instances, the anode precursor is fabricated using one, two, three, four, five or six parameters selected from the group consisting of a laser pulse duration, pulse frequency, power density, scan rate, pass interval, and pass number. In these instances, the laser pulse duration is 400 femtoseconds, the laser pulse frequency is 400 kHz, the power density is $7.99 \times 10^{11}$ W/cm$^2$, the scan rate is 720 mm/sec, the pass interval is 0.25 s, and the pass number is 60.

Using a laser to extract the one or more anode precursors 56 from the sheet of material 48 can convert at least a portion of the first phase of the anode metal oxide 12 to a second phase of the anode metal oxide 12. For instance, using a laser to cut a sheet of material 48 with aluminum as the anode metal 14 and the boehmite phase of aluminum oxide (AlO(OH)) as the anode metal oxide 12 can convert the boehmite phase of aluminum oxide to the alpha-corundum oxide ($\alpha$-Al$_2$O$_3$) phase of aluminum oxide. This conversion is believed to be a result of the heat generated during the laser cutting process. As a result, the conversion primarily occurs at and/or near the edge of the anode precursor 56. The second phase of the anode metal oxide 12 is often undesirable. For instance, the second phase of the anode metal oxide 12 can be more electrically conductive than the first phase of the anode metal oxide 12. As an example, the alpha corundum oxide ($\alpha$-Al$_2$O$_3$) phase of aluminum oxide has properties of a semiconductor. As a result, the alpha phase corundum oxide ($\alpha$-Al$_2$O$_3$) is not suitable for use as a dielectric and is accordingly associated with undesirably high levels of leakage and deformation. However, alpha phase corundum oxide ($\alpha$-Al$_2$O$_3$) is very stable and is difficult to convert back into the boehmite phase of aluminum oxide. While adjustments to the laser cutting parameters disclosed above can partially address the leakage and deformation associated with the this conversion from the first phase of the anode metal oxide to the second phase of the anode metal oxide, an oxide extraction phase discussed in more detail below can further reduce the leakage and deformation caused by this conversion.

The process of extracting the anode precursor 56 from the sheet of material 48 can leave the anode metal 14 exposed at the edges of the anode precursor 56. In some instances, a hydration layer is optionally formed on the exposed anode metal 14. The hydration process builds a non-voltage supporting hydration layer that helps to both create a higher quality anode metal oxide 12 and speed up its formation during a subsequent aging process. The hydration process lowers the aging time by using a hydration oxide backbone to speed formation of the anode metal oxide 12 during aging. In some instances, the hydration process cleans up the edges of anode precursor 56 by "smoothing" any metal burrs on the edges. The detachment of the burrs and "smoothing" can be increased by use of sonic or ultrasonic vibrational energy when forming the hydration layer.

A suitable method of creating the hydration layer includes, but is not limited to, immersing at least a portion of the anode precursor 56 in a bath the includes, consists of, or consists essentially of water. In one example, the water is de-ionized. The bath may be held at a temperature between 60 and 100 degrees C., and preferably at about 95 degrees C. The anode precursor 56 may remain immersed in the bath for a period of time greater than 2 minutes and/or less than 20 minutes to form the hydration layer. In some instances, the bath is sonicated at either sonic or ultrasonic frequencies. The formation of the hydration layer will help to form a better quality oxide during a subsequent aging process.

A passivation layer can optionally be formed on the exposed anode metal that is not covered by the anode metal oxide or the hydrate of the anode metal. A suitable method for forming the passivation layer includes, but is not limited to, immersing at least a portion of the anode precursor 56 in a second bath that includes, consists of, or consists essentially of ammonium dihydrogen phosphate. In some instances, the second bath is maintained at a temperature greater than 51° C. and/or less than 90° C., or 70° C. Additionally or alternatively, the second bath can contain more than 0.1 wt %, or 5.0 wt %, and/or less than 2.2 wt % ammonium dihydrogen phosphate. The anode precursor 56 can be at least partially immersed in the second bath for a time greater than one minutes and/or less than four minutes. After removing the anode precursor 56 from the second bath, the anode precursor 56 can be rinsed under de-ionized water for a time greater than one minute and/or less than 12 minutes.

The one or more anode precursors 56 constructed according to FIG. 2A through FIG. 2H are included in a capacitor precursor 61 according to FIG. 2J. For instance, one or more of the anode precursors 56 are combined with one or more separators 24 and one or more cathodes 16 so as to firm an electrode assembly 22 with the components arranged as disclosed in the context of FIG. 1A through FIG. 1E. The electrode assembly 22 is placed in a capacitor case 26 along with the electrolyte 40. Any electrical connections needed for operation of the capacitor precursor 61 are made and the capacitor case 26 is sealed.

Although not shown in FIG. 2A through FIG. 2J, one or more masks can be placed on the sheet of material before fabricating the preliminary channels in the sheet of material 48. The masks can be positioned to protect areas of the sheet of material from formation of the channels. For instance, the electrodes often have one or more inactive areas that are attached to electrical conductors such as tabs that provide electrical communication between the electrodes and a capacitor terminal. These inactive areas can be masked before fabricating the preliminary channels and the mask(s) can be removed after forming the preliminary channels 52 in the sheet of material 48 or after widening of the preliminary channels 52. In some instances, the mask(s) are removed before the anode metal oxide 12 is formed on the anode metal 14.

The capacitor precursor 61 can optionally be put through an aging phase configured to form an anode metal oxide 12 on the edges on the one or more anode precursors 56 in the capacitor and/or on any other exposed anode metal 14. The capacitor precursor 61 can optionally be put through a testing phase configured to test the capacitor precursor 61 for charge and discharge functionality.

Example 1

A first bath was prepared and was 75 ppm molybdic acid, 0.62 wt. % hydrochloric acid, 0.92 wt. % sulfuric acid, 3.5 wt. % sodium perchlorate, 60 ppm nonafluorobutanesulfonic acid (FBSA), with a pH of 0.5 at 80° C. A first aluminum foil was used as a sheet of material and placed in the first bath for a chemical etch duration of 15 seconds. Upon expiration of the chemical etch duration, the aluminum foil was electrochemically etched in the same bath at 80° C. for 2 minutes at a current of 0.25 to 0.3 amps/cm$^2$. The resulting channels were widened electrochemically. The anode metal oxide was formed in the channels at 490 Volts.

A second bath was prepared and was 0.62 wt. % hydrochloric acid, 0.92 wt. % sulfuric acid, 3.5 wt. % sodium perchlorate, 60 ppm nonafluorobutanesulfonic acid (FBSA), with a pH of 0.5 at 80° C. A second aluminum foil was used as a sheet of material and placed in the second bath and electrochemically etched in the second bath at 80° C. for 2 minutes at a current of 0.25 to 0.3 amps/cm$^2$. The second aluminum foils was not chemically etched before the electrochemical etch. The resulting channels were widened electrochemically. The anode metal oxide was formed in the channels at 490 Volts.

The average sheet capacitance resulting from the second aluminum foil was 334 microF and the average sheet capacitance resulting from the first aluminum foil was 356 microF indicating a 6.6% increase in foil capacitance.

First capacitors were built with anodes that included aluminum from the first aluminum foil and second capacitors were built with anodes that included aluminum from the second aluminum foil. The first capacitors showed a 4.0% increase in delivered energy over the second capacitors.

Example 2

An etch bath was prepared that was 75 ppm molybdic acid, 0.62 wt. % hydrochloric acid, 0.92 wt. % sulfuric acid, 3.5 wt. % sodium perchlorate, 60 ppm nonafluorobutanesulfonic acid (FBSA), with a pH of 0.5 at 80° C. Multiple different aluminum foils were each used as a sheet of material and placed in the etch bath for different chemical etch durations. Upon expiration of each chemical etch duration, the aluminum foil was electrochemically etched in the same bath at 80° C. for 2 minutes at a current of 0.25 to 0.3 amps/cm$^2$. The resulting channels were widened electrochemically. The anode metal oxide was formed in the channels at 490 Volts.

A control etch bath was prepared that was 75 ppm molybdic acid, 0.62 wt. % hydrochloric acid, 0.92 wt. % sulfuric acid, 3.5 wt. % sodium perchlorate, 60 ppm nonafluorobutanesulfonic acid (FBSA), with a pH of 0.5 at 80° C. Multiple different control aluminum foils were each used as a sheet of material and placed in the control bath and electrochemically etched at 80° C. for 2 minutes at a current of 0.25 to 0.3 amps/cm$^2$. The resulting channels were widened electrochemically. The anode metal oxide was formed in the channels at 490 Volts.

The aluminum foils that were chemically etched for a chemical etch duration of 30 seconds showed an average foil capacitance of 366.1 microF. The aluminum foils that were chemically etched for a chemical etch duration of 22 seconds showed an average foil capacitance of 369.1 microF. The aluminum foils that were chemically etched for a chemical etch duration of 15 seconds showed an average foil capacitance of 371.96 microF. The aluminum foils that were chemically etched for a chemical etch duration of 7 seconds showed an average foil capacitance of 377.72 microF. In comparison the control aluminum foils was not chemically etched before the electrochemical etch and had an average foil capacitance of 340 microF.

Figure 3:
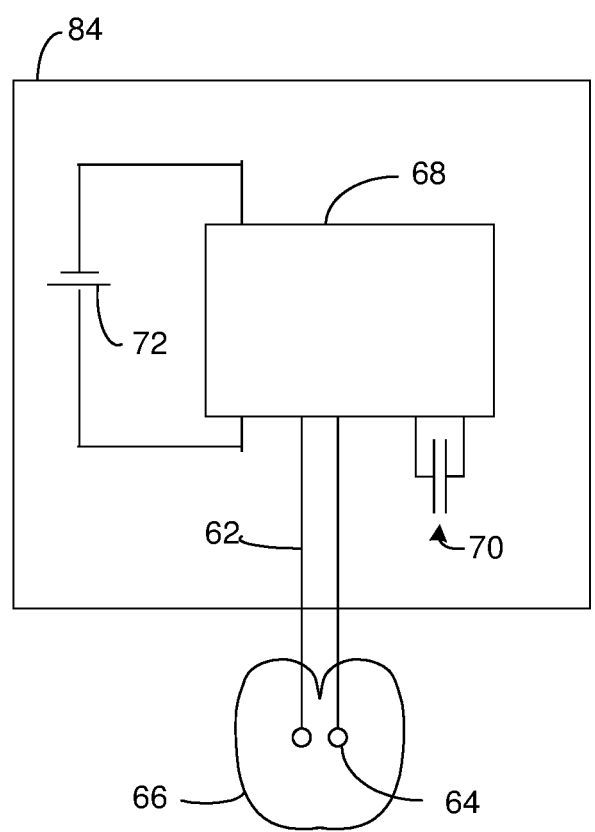
FIG. 3 is a schematic diagram of a defibrillation system that includes an Implantable Cardioverter Defibrillator (ICD) that employs one or more capacitors.

FIG. 3 is a schematic diagram of a defibrillation system that includes an Implantable Cardioverter Defibrillator (ICD) that employs one or more capacitors constructed as disclosed above. The defibrillation system includes lead lines 62 connected to electrodes 64 in contact with the heart. Although the defibrillation system is shown with two electrodes 64, the defibrillation system may include three or more electrodes 64 and/or three or more lead lines. The specific positions of the electrodes 64 relative to the heart 66 is dependent upon the requirements of the patient.

The defibrillation system also includes a processing unit 68. The lead lines 62 provide electrical communication between the processing unit 68 and the electrodes 64. The processing unit 68 is also in electrical communication with one or more capacitors constructed as disclosed above.

The processing unit 68 receives power from a battery 72. The processing unit 68 can place the battery 72 in electrical communication with the one or more capacitors 70. For instance, the processing unit 68 can cause the battery 72 to charge the one or more capacitors 70. Additionally, the processing unit 68 can place the one or more capacitors 70 in electrical communication with the lead lines 62. For instance, the processing unit 68 can cause the one or more capacitors to be discharged such that electrical energy stored in the one or more capacitors is delivered to the heart through all or a portion of the electrodes 64. The processing unit 68, the battery 72 and the one or more capacitors 70 are positioned in a case 84.

During operation of the defibrillation system, the defibrillation system employs output from the lead lines 62 to monitor the heart and diagnose when defibrillation shocks should be provided. When the processing unit 68 identifies that defibrillation shocks are needed, the processing unit 68 provides the heart with one or more defibrillation shocks. To provide a defibrillation shock, the processing unit 68 employs energy from the battery 72 to charge the one or more capacitors 70. Once the one or more capacitors are charged, the processing unit 68 causes these capacitors to be discharged such that energy stored in the capacitors is delivered to the heart through all or a portion of the electrodes 64 in the form of defibrillation shocks. During the defibrillation shocks, the defibrillator requires that one or more pulses be delivered from the battery 72 to the one or more capacitors. Each pulse is generally associated with a defibrillation shock. The duration of each pulse is generally about 8 to 12 seconds with the pulses separated by a delay time that is based on how fast the battery charges the capacitor and determining the appropriate point to provide the defibrillation shock.

Suitable electronics 68 can include, but are not limited to, analog electrical circuits, digital electrical circuits, processors, microprocessors, digital signal processors (DSPs), computers, microcomputers, or combinations suitable for performing the monitoring and control functions. In some instances, the electronics 68 has access to a memory that includes instructions to be executed by the electronics 68 during performance of the control and monitoring functions.

The sequence of events disclosed above for forming an anode can be performed in a sequence other than the disclosed sequence. For instance, the oxide phase extraction can be performed on the anode before the capacitor is assembled. As another example, the aging phase can be performed after the testing phase.

Although the above methods of forming an anode have been disclosed in the context of a capacitor, the above oxide phase extraction can also be applied to the fabrication of anodes, cathodes, positive electrodes, and/or negative electrodes in batteries.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. A method fabricating a capacitor by increasing a surface area of a sheet of material, comprising:
   performing a chemical etch on the sheet of material, wherein the chemical etch includes immersing the sheet of material in a chemical etch bath, the chemical etch bath includes molybdenum and has a pH greater than 0.0 and less than or equal to 2.5;
   performing an electrochemical etch on the sheet of material after performing the chemical etch on the sheet of material, wherein the electrochemical etch including immersing the sheet of material in an electrochemical etch bath, the electrochemical etch bath includes molybdenum and has a pH greater than 0.0 and less than or equal to 2.5; and
   extracting an electrode from the sheet of material after performing the electrochemical etch on the sheet of material.

2. The method of claim 1, wherein the chemical etch is performed for less than 45 seconds.

3. The method of claim 1, wherein the chemical etch is performed for a time period between 0 seconds and 20 seconds.

4. The method of claim 1, wherein the molybdenum included in the chemical etch bath is in element form or is included in a compound.

5. The method of claim 4, wherein the molybdenum is included in a chemical component selected from the group consisting of molybdic acid, molybdenum trioxide, sodium molybdate dihydrate, molybdenum (V) chloride, molybdenum sulfide, molybdenum (IV) dioxide, and molybdenum (II) chloride.

6. The method of claim 1, wherein the molybdenum included in the electrochemical etch bath is in elemental form or is included in a compound.

7. The method of claim 6, wherein the molybdenum is included in a chemical component selected from the group consisting of molybdic acid, molybdenum trioxide, sodium molybdate dihydrate, molybdenum (V) chloride, molybdenum sulfide, molybdenum (IV) dioxide, and molybdenum (II) chloride.

8. The method of claim 1, wherein the chemical etch includes immersing at least a portion of the sheet of material in an etch bath and the electrochemical etch includes immersing at least a portion of the sheet of material in the same etch bath.

9. The method of claim 8, wherein the sheet of material is not removed from the etch bath between the chemical etch and the electrochemical etch.

10. The method of claim 9, wherein an electrical potential is not applied across the sheet of material during the chemical etch but is applied during the electrochemical etch or an electrical potential applied across the sheet of material during the chemical etch is less than 5% of the electrical potential applied across the sheet of material during the electrochemical etch.

11. The method of claim 9, wherein an electrical current is not passed through the sheet of material during the chemical etch but does flow through the sheet of material during the electrochemical etch or an electrical current is passed through the sheet of material during the chemical etch at less than 5% of an electrical current passed through the sheet of material during the electrochemical etch.

12. The method of claim 9, wherein the chemical etch is performed for less than 45 seconds.

13. The method of claim 12, wherein the chemical etch is performed for a time period between 0 seconds and 15 second.

* * * * *